US010953084B2

United States Patent
Sno et al.

(10) Patent No.: US 10,953,084 B2
(45) Date of Patent: Mar. 23, 2021

(54) COMBINATION VACCINE AGAINST PCV2 AND PRRS VIRUS INFECTION COMPRISING ALBUMIN

(71) Applicant: Intervet Inc., Madison, NJ (US)

(72) Inventors: Melanie Sno, Venlo (NL); Pieter Van Gelder, St. Anthonis (NL); Vicky Fachinger, Bad Soden (DE); Chen Shu-hui Tan, Amsterdam (NL)

(73) Assignee: Intervet Inc., Madison, NJ (US)

( * ) Notice: Subject to any disclaimer, the term of this patent is extended or adjusted under 35 U.S.C. 154(b) by 91 days.

(21) Appl. No.: 16/086,629

(22) PCT Filed: Mar. 22, 2017

(86) PCT No.: PCT/EP2017/056801
§ 371 (c)(1),
(2) Date: Sep. 20, 2018

(87) PCT Pub. No.: WO2017/162727
PCT Pub. Date: Sep. 28, 2017

(65) Prior Publication Data
US 2019/0091321 A1 Mar. 28, 2019

(30) Foreign Application Priority Data

Mar. 23, 2016 (EP) ..................... 16161982

(51) Int. Cl.
| | | |
|---|---|---|
| *A61K 39/12* | (2006.01) | |
| *A61K 39/00* | (2006.01) | |
| *C12N 7/00* | (2006.01) | |
| *C07K 14/005* | (2006.01) | |
| *A61K 39/02* | (2006.01) | |

(52) U.S. Cl.
CPC .......... *A61K 39/12* (2013.01); *A61K 39/0241* (2013.01); *A61K 2039/521* (2013.01); *A61K 2039/5254* (2013.01); *A61K 2039/54* (2013.01); *A61K 2039/55* (2013.01); *A61K 2039/552* (2013.01); *A61K 2039/70* (2013.01); *C12N 2750/10034* (2013.01); *C12N 2770/10034* (2013.01)

(58) Field of Classification Search
CPC .............. A61K 39/12; A61K 2039/552; C12N 2750/10034; A61P 31/12; A61P 31/20
See application file for complete search history.

(56) References Cited

U.S. PATENT DOCUMENTS

| | | | |
|---|---|---|---|
| 8,728,487 B2 | 5/2014 | Wu et al. | |
| 2013/0266601 A1* | 10/2013 | Galvin | ............... A61P 31/12 424/186.1 |
| 2014/0322267 A1 | 10/2014 | Haiwick | |

FOREIGN PATENT DOCUMENTS

| | | |
|---|---|---|
| WO | 2006074986 A2 | 7/2006 |
| WO | 2007028823 A1 | 3/2007 |
| WO | 2007094893 A2 | 8/2007 |
| WO | 2008076915 A2 | 6/2008 |
| WO | 2014048955 A1 | 4/2014 |
| WO | 2015124594 A1 | 8/2015 |

OTHER PUBLICATIONS

Morioka et al., "Effect of the serum albumin on replication of porcine reproductive and respiratory syndrome virus in a cell culture", Acta Virologica, 51, 2007:289-290.*
Extended European Search Report for Application 16161982 dated Sep. 29, 2016.
Himmler, C et al., Comparison of reproductive parameters in sows vaccinated intradermally or intramuscularly with a modified live porcine reproductive and respiratory syndrome virus (PRRSV) vaccine, in consideration of parity and season, : Database Biosis (online); Biosciences Information Service, 2013, Tieraerztliche Umschau, 61-65; BIOSIS XP002761605, 68(3).
InternationalSearch Report for appl. PCTEP2017056801, dated Jun. 12, 2017, 4 sheets.
Morioka, K et al, Effect of the serum albumin on replication of porcine reproductive and respiratory syndrome virus in a cell culture, Acta virologica, Jan. 1, 2007, pp. 289, vol. 52, No. 4.

* cited by examiner

*Primary Examiner* — Barry A Chestnut
(74) *Attorney, Agent, or Firm* — Sarah L. Hooson; Catherine D. Fitch

(57) ABSTRACT

The present invention pertains to a vaccine for use in prophylactically treating an animal against an infection with porcine circovirus type 2 (PCV2) and an infection with PRRS virus, the vaccine comprising in combination non-replicating immunogen of porcine circovirus type 2 and live attenuated PRRS virus, wherein the vaccine additionally comprises albumin.

15 Claims, 3 Drawing Sheets

COMBINATION VACCINE AGAINST PCV2 AND PRRS VIRUS INFECTION COMPRISING ALBUMIN

CROSS-REFERENCE TO RELATED APPLICATIONS

This application is a national stage entry under 35 U.S.C. § 371 of PCT/EP2017/056801 filed on Mar. 22, 2017, which claims priority to EP16161982.0 filed on Mar. 23, 2016, the contents of which are hereby incorporated by reference in their entireties.

GENERAL FIELD OF THE INVENTION

The invention in general pertains to the field of swine health. Swine are prone to many pathogenic micro-organisms. Control of infection is commonly done by stable and feed management, treatment with pharmaceuticals such as anti-viral drugs and antibiotics, or prophylactic treatment using vaccines. In particular, the invention pertains a vaccine against porcine circo virus type 2 (PCV-2) and PRRS (porcine reproductive and respiratory syndrome) virus, and to a method of protecting an animal against such infections using the vaccine.

BACKGROUND ART

PCV2 and PRRS virus are two viruses that give rise to significant economic losses in the swine industry. PCV-2 is linked to the post-weaning multisystemic wasting syndrome (PMWS) observed in young pigs. This disease was encountered for the first time in Canada in 1991. The clinical signs and pathology were published in 1996, and include progressive wasting, dyspnea, tachypnea, and occasionally icterus and jaundice. Nayar et al., Can. Vet. J. Volume 38, June 1997 detected porcine circo virus in pigs with clinical symptoms of PMWS and concluded that a PCV, other than the known PCV recognized as a natural inhabitant of PK-15 cells, could be linked to PMWS. Later publications (Hamel et al., J. Virol., 72(6), 5262-5267, 1998; Meehan et al., J. gen. Virol., 79, 2171-2179, 1998) confirmed these findings, and it was proposed (Meehan et al., supra) to refer to the new pathogenic PCV as PCV-2, whereas the original PK-15 cell culture isolate (Tischer et al., Nature 295, 64-66, 1982), should be referred to as PCV-1. PCV-2 is a small (17-22 nm) icosahedral non-enveloped virus containing a circular single stranded DNA genome. The length of the PCV-2 genome is about 1768 bp. PCV-2 isolates originating from different regions in the world seem to be closely related to each other and display 95 to 99% nucleotide sequence identities (Fenaux et al., J. Clin. Micorbiol., 38(7), 2494-2503, 2000). ORF-2 of PCV encodes the capsid protein of the virus. The ORF 2 of PCV 2 encodes a protein of about 233 amino acids. The ORF 2 of all PCV-2 isolates share 91-100% nucleotide sequence identity and 90-100% deduced amino acid sequence identity.

PRRS virus first reported in 1987 in North America and Central Europe. PRRS virus is a small, enveloped RNA virus. It contains a single-stranded, positive-sense, RNA genome with a size of approximately 15 kilobases. The genome contains nine open reading frames. The virus is a member of the genus Arterivirus, family Arteriviridae, order Nidovirales. The two prototype strains of PRRSV are the North American strain, VR-2332, and the European strain, the Lelystad virus (LV). The European and North American PRRSV strains cause similar clinical symptoms. In the early 2000s a highly pathogenic strain of the North American genotype emerged in China. This strain, HP-PRRSV, is more virulent than all other strains, and causes great losses in Asian countries worldwide. For any PRRS virus, subclinical infections are common, with clinical signs occurring only sporadically in a herd. Clinical signs include reproductive failure in sows such as abortions and giving birth to stillborn or mummified fetuses, and cyanosis of the ear and vulva. In neonatal pigs, the disease causes respiratory distress, with increased susceptibility to respiratory infections such as Glasser's disease.

Vaccines against the above identified pathogens are commonly known. A conventional vaccine to prophylactically treat animals, in particular pigs, against an infection with PCV 2, may be based on whole inactivated PCV-2 virus as (non-replicating) immunogen. Also, in the art it has been shown that the ORF2 encoded capsid protein (e.g. when recombinantly expressed) is suitable as a subunit immunogen of porcine circo virus type 2 for use in an adequate vaccine. This can be understood since this subunit, in a circulatory system, shows up the same way as the virus itself, essentially differing in the fact that the DNA and non-structural proteins are not present inside the capsid. In the art several vaccines against PCV2 are commercially available. Porcilis® PCV (available from MSD Animal Health, Boxmeer, The Netherlands) is a vaccine for protection of pigs against porcine circo virus type 2, for use in pigs from three weeks and older. When given as a two-shot (two dose) vaccine, the duration of immunity (DOI) is 22 weeks, almost completely covering the fattening period of pigs. Ingelvac CicroFlex® (available from Boehringer Ingelheim, Ingelheim) is a vaccine for protection of pigs against porcine circo virus type 2, for use in pigs from two weeks and older. It is registered as a one-shot (one dose) vaccine only. Circovac® (available from Merial, Lyon, France) is a vaccine for protection of pigs against porcine circo virus type 2, for use in pigs three weeks and older. Suvaxyn® PCV (available from Zoeitis, Capelle a/d IJssel, The Netherlands) is a vaccine for protection of pigs against porcine circo virus type 2, for use in pigs from three weeks and older. Other PCV2 vaccines are described for example in WO2007/028823, WO 2007/094893 and WO2008/076915.

Regarding PRRS virus, although inactivated virus vaccines have been described and are commercially available, modified Live Vaccines (MLV) vaccines comprising either the European type (type I) or the North American type (type II) in live attenuated form, are the primary immunological tool for its control. Several vaccines are commercially available in the art. Porcilis® PRRS (available from MSD Animal Health, Boxmeer, The Netherlands) is a vaccine comprising live attenuated PRRS virus type I and is registered to reduce infection (viraemia) caused by infection with PRRS virus. Ingelvac PRRS® MLV (available from Boehringer Ingelheim, Ingelheim) is a vaccine that aids in the reduction of disease caused by PRRS virus and which vaccine provides cross protection against strains of different types. Fostera® PRRS (available from Zoeitis, Florham Park, N.J., USA) is also a MLV vaccine and is registered for protection against both the respiratory and reproductive forms of disease caused by PRRS virus. Other PRRS vaccines are described for example in WO2006/074986, U.S. Pat. No. 8,728,487 and WO2014/048955.

OBJECT OF THE INVENTION

There is a continuous need for convenient, safe and efficacious means for the management of swine health. The object of the invention is to provide a vaccine that meets this need, in particular the need for a novel PCV2/PRRS virus combination vaccine.

SUMMARY OF THE INVENTION

In order to meet the object of the invention, a new vaccine has been devised, the vaccine comprising in combination non-replicating immunogen of porcine circo virus type 2 and live attenuated PRRS virus, wherein the vaccine in addition to the immunogens comprises albumin (i.e. any of the water-soluble, heat denaturable, non glycosylated globular proteins, found i.a. in serum and egg-white).

Although for both viruses vaccines are known and commercially available, and even the combination of these immunogens has been shown in the art, there is a constant need for improvements in particular leading to a vaccine which is efficacious and at the same time safe for use in young animals. It was applicant's recognition that the PCV subunit vaccine might interfere with the live PRRS virus to suppress its viability. This may lead to a reduced efficacy of the PRRS virus component in a combination vaccine. By adding albumin to the combination vaccine, the suppression of the PRRS virus viability appears to be reduced.

As is commonly known, not all combinations of antigens contemplated or suggested may lead to a safe and optimally effective combination vaccine. In fact, there is a high level of uncertainty with regard to safety and efficacy of any combination vaccine, even when the single (monovalent) vaccines are safe and efficacious.

The committee for veterinary medicinal products of the European Agency for the Evaluation of Medicinal Products (EMEA) in its publication "Note for guidance: requirements for combined veterinary products" (EMEA, 2000, CVMP/IWP/52/97-FINAL), stated (page 2/6) that the "development of combined vaccines is not straightforward. Each combination should be developed and studied individually in terms of quality, safety and efficacy". The committee further indicates that the search for a good combination vaccine typically includes the compatibility between the individual components in the combined vaccine, including for example preservatives, excipients and stabilisers, inactivating agents and adjuvants. On page 3, top paragraph, it is stated that "In combined vaccines, the presence of more than one component can often cause an interaction, leading to either a diminished or an increased response to individual components, compared to when the specific component(s) is administered alone . . . . Such interactions are often immunological in nature, but may also be caused by other factors with less direct effects on the immune system", and also "When an adjuvant is used to augment the immune response to a combined vaccine, special problems may appear."

The U.S. Department of Health and Human Services, Food and Drug Administration, Center for Biologics Evaluation and Research, published in April 1997 a "Guidance for Industry, for the evaluation of combination vaccines for preventable diseases: Production, Testing and Clinical Studies", in which guidance it is stated (page 3, under "Compatibility of Components") that "Experience has shown that combining monovalent vaccines may result in a new combination which is less safe or effective than desirable. Sometimes the components of inactivated vaccines may act adversely on one or more of the active components", indicating that especially an inactivated vaccine may negatively influence the efficacy of a live vaccine, such as for example occurred when combining a live pertussis vaccine and an inactivated poliovirus vaccine that resulted in a vaccine with decreased pertussis potency. It is indicated that any additional components in the vaccine might complicate the safety and potency of the final product when compared to the individual vaccines.

The World Health Organization (WHO) has published an e-learning course called "Vaccine Safety Basics", which in the MODULE 2 contemplates combination vaccines. This module starts with "Licensed combination vaccines undergo extensive testing before approval by national authorities to assure that the products are safe, effective, and of acceptable quality." It is also stated that "With all combinations, manufacturers must therefore evaluate the potency of each antigenic component, the effectiveness of the vaccine components when combined to induce immunity, risk of possible reversion to toxicity, and reaction with other vaccine components."

All in all, it is commonly known that the development of a combination vaccine is not straightforward and requires experimentation to determine safety and efficacy.

The present invention also pertains to a vaccine for use in prophylactically treating an animal against an infection with porcine circovirus type 2 (PCV2) and an infection with PRRS virus, the vaccine comprising in combination non-replicating immunogen of porcine circo virus type 2 and live attenuated PRRS virus, wherein the vaccine comprises albumin.

In addition, the present invention also pertains to a method for prophylactically treating an animal against an infection with porcine circovirus type 2 (PCV2) and an infection with PRRS virus by administrating to the animal a vaccine comprising in combination non-replicating immunogen of PCV2, live attenuated PRRS virus and albumin. The invention also pertains to the use of non-replicating immunogen of porcine circo virus type 2 (PCV2) and live attenuated PRRS virus to manufacture a vaccine comprising in combination the immunogen of PCV2, the live attenuated PRRS virus and albumin, for administration to an animal to prophylactically treat the animal against an infection with PCV2 and an infection with PRRS virus.

It is noted that in a vaccine the immunogen (also called antigen) is typically combined with a pharmaceutically acceptable carrier, i.e. a biocompatible medium, viz. a medium that after administration does not induce significant adverse reactions in the subject animal, capable of presenting the immunogen to the immune system of the host animal after administration of the vaccine, such as a liquid containing water and/or any other biocompatible solvent or a solid carrier such as commonly used to obtain freeze-dried vaccines (based on sugars and/or proteins), optionally comprising immunostimulating agents (adjuvants), which upon administration to the animal induces an immune response for treating an animal against an infection with a wild-type micro-organism, i.e. for aiding in preventing, ameliorating or curing such infection or a disorder arising therefrom. Optionally other substances such as stabilisers, viscosity modifiers or other components are added depending on the intended use or required properties of the vaccine.

Definitions

Figure 1:
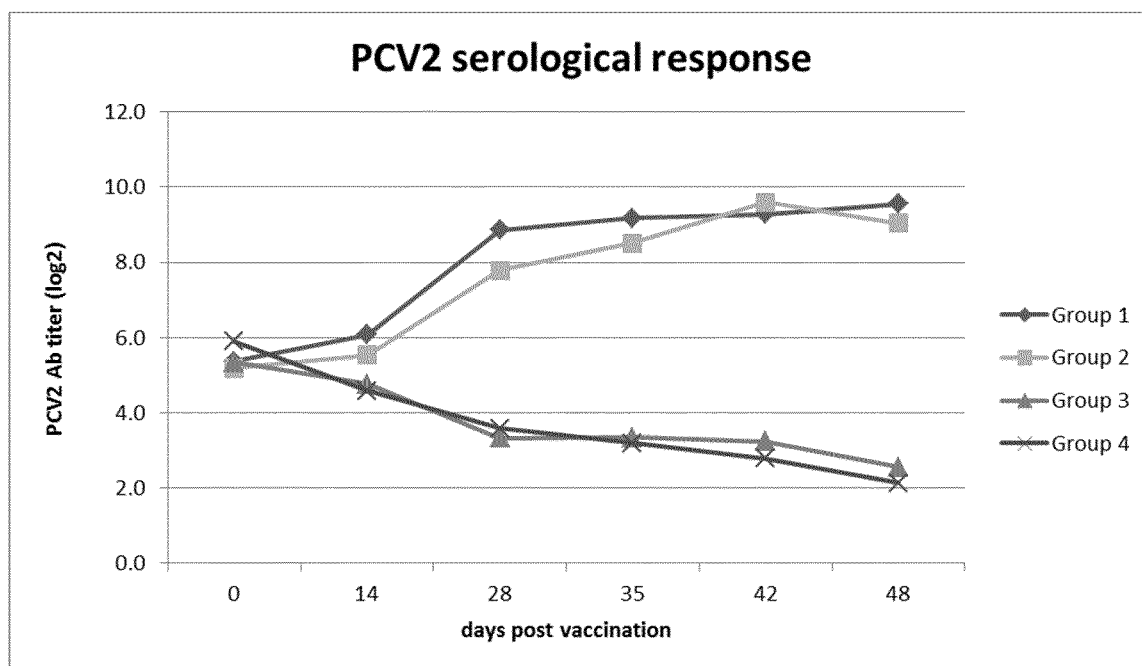
FIG. 1 is a line graph representing the PCV2 serological response.

A vaccine is a pharmaceutical composition that is safe to administer to a subject animal, and is able to induce protective immunity in that animal against a pathogenic microorganism, i.e. to induce a successful prophylactic treatment as defined here below.

Non-replicating immunogen of a pathogen is any substance or compound corresponding to the pathogen, other than the live replicating pathogen as a whole (either in wild type of attenuated form), against which pathogen an immunological response is to be elicited, such that the corresponding virulent pathogen or one or more of its virulence factors will be recognized by the host's immune system as a result of this immune response and are ultimately at least partly neutralized. Typical examples of non-replicating immunogens are killed whole pathogens and subunits of these pathogens such as capsid proteins and surface expressed proteins, for example recombinantly expressed proteins.

Prophylactic treatment against an infection with a pathogen is aiding in preventing or ameliorating an infection with that pathogen or a disorder arising from that infection, resulting from a post treatment challenge with a pathogenic pathogen, in particular to reduce its load in the host after such challenge and optionally to aid in preventing or ameliorating one or more clinical manifestations resulting from the post treatment infection with the pathogen.

A live attenuated pathogen is a viable, replication competent (viable) form of the pathogen having reduced virulence. The process of attenuation takes an infectious pathogen and alters it so that it becomes harmless or less virulent, typically by either multiple passages of the pathogen through cell systems or by genetically modifying the pathogen.

Single dose administration of a vaccine for use in prophylactically treatment means that in order to arrive at protective immunity, the vaccination does not need to be boosted with a second administration of the vaccine. In a two-shot regime, the first (prime) vaccination is typically boosted within 6 weeks from the first administration, commonly within 3 or even 2 weeks from the first administration, and only after the second (boost) administration protective immunity, i.e. a successful prophylactic treatment as defined here above, may be obtained.

EMBODIMENTS OF THE INVENTION

In a first embodiment of the vaccine according to the invention per se, the vaccine comprises ovalbumin. Ovalbumin (i.e. albumin derivable from egg-white) appeared to be suitable to suppress the reduction of PRRS virus viability, and as opposed to for example bovine albumin, has less safety issues involved (in particular the non-presence of prion proteins associated with bovine spongiform encephalopathy).

In a second embodiment, the albumin concentration is between 1 and 10% (w/w). Experimentally, amounts of 0.3%, 1% and 3% of the albumin were found to be practically feasible. Based on the noticed effect and the solubility of albumin, it is believed that an optimal concentration is between 0.1 and 10% (weight of albumin over weight of the total vaccine). In particular, any amount of 0.1, 0.2, 0.3, 0.4, . . . 1, 2, 3, 4, 5, 6, 7, 8, 9 or 10% w/w (and any intervening amount) may be used in this embodiment.

In another embodiment the non-replicating immunogen of PCV2 is recombinantly expressed ORF2 protein of PCV2. This recombinant protein has proven to be suitable for application in the present invention. In particular, the ORF2 protein can be expressed in a baculo virus expression system such as described in WO2007/028823, WO 2007/094893 or WO2008/076915.

In still another embodiment the vaccine comprises in addition non-replicating immunogen of *Mycoplasma hyopneumoniae* (*M. hyo*) In this embodiment the vaccine is capable of providing protection against three major swine pathogens by using just one vaccine. Many commercial vaccines against *M. hyo* exist and these are routinely used in the majority of commercial swine farming operations. Generally these vaccines comprise non-replicating immunogens such as subunit proteins and/or bacterins (i.e. a composition comprising killed bacteria, either as whole cells, (partly) lysed, homogenised, French pressed, a combination of this or comprising the killed bacteria in another form as long as the composition is derived from a killed bacterial culture) which are typically administered by parenteral injection. Some examples are: RespiSure® (Zoetis), Ingelvac® *M. hyo*, and MycoFLEX® (Boehringer Ingelheim), Hyoresp® (Merial), Stellamune® *Mycoplasma* (Elanco Animal Health), Fostera® PCV MH (Zoetis) and M+Pac® (MSD Animal Health).

In a first embodiment of the specific use of a vaccine according to the invention the vaccine is for administration into the dermis of the animal. Even though it is already not easy to devise a new combination vaccine per se, devising a combination vaccine for a particular site of administration is even less straightforward. The World Health Organization (WHO) for example has published an e-learning course called "Vaccine Safety Basics", in which course on page 53 it is reported that "The route of administration is the path by which a vaccine (or drug) is brought into contact with the body. This is a critical factor for success of the immunization. A substance must be transported from the site of entry to the part of the body where its action is desired to take place. Using the body's transport mechanisms for this purpose, however, is not trivial."

In this respect the California Department of Health Services' Immunization Branch has published guidelines for correct immunization (www.cdc.gov/vaccines/pubs/pinkbook/downloads/appendices/d/vacc_admin.pdf). With regard to the administration site it is stated on page 7, first full paragraph that "The recommended route and site for each vaccine are based on clinical trials, practical experience and theoretical considerations. This information is included in the manufacturer's product information for each vaccine. There are five routes used in the administration of vaccines. Deviation from the recommended route may reduce vaccine efficacy or increase local adverse reactions." On page 14 the only US-licensed intradermal vaccine is addressed: "Fluzone Intradermal is the only US-licensed vaccine that is administered by the intradermal route. It is approved only for use in persons 18 through 64 years of age. This Fluzone formulation is not the same as intramuscular formulations of inactivated influenza vaccine (TIV). Other TIV formulations should NOT be administered by the intradermal route."

Regarding intradermal administration, although intradermal administration is often carried out using a needle-less vaccination device such as the IDAL® vaccinator (available from MSD Animal Health, Boxmeer, The Netherlands), "intradermal" administration per se should not be equated with "needle-less" administration. The World health Organization in its Aug. 27, 2009 paper titled "Intradermal Delivery of Vaccines; A review of the literature and the potential for development for use in low- and middle-income countries" indeed clearly indicates that "needle-less" vaccination does not necessarily mean "intradermal" vaccination (see Table 1, Page 3 of the review). Only when a needle-less device is "configured for intradermal vaccination", then a vaccine may indeed be delivered (at least partly) into the dermis. Otherwise the vaccine may be delivered subcutaneous or intramuscularly in its entirety.

In a second embodiment of the specific use of a vaccine according to the invention the vaccine is administered by a single dose. It was found that a single dose administration led to an effective vaccine. This provides for a very convenient and economical way to protect animals against both pathogenic viruses.

In a next embodiment of the specific use of a vaccine according to the invention, the vaccine is administered with a needle-less vaccination device, using a jet of the vaccine to reach the dermis through the skin of the animal. Vaccination into the dermis is in this embodiment provided by a needle-less vaccination device using a liquid jet of the vaccine (a high pressurized fluid stream), typically using a very low volume of vaccine in the range of 0.05 to 0.2 ml. This further increases the safety of the vaccine and method of administration.

In yet another embodiment of the specific use of a vaccine according to the invention, the immunogen of PCV2 and the live attenuated PRRS virus are combined in the vaccine within 24 hours, preferably within 6 hours before administration. Combining the antigens right before administration provides more freedom to choose the excipients since stability of the vaccine might still not be straightforward to achieve, at least not for any and all pharmaceutically acceptable carrier compositions.

In still another embodiment of the specific use of a vaccine according to the invention, before combination of the immunogens, the albumin is present in combination with the immunogen of PRRS virus.

The invention will now be explained further using the following examples.

EXAMPLES

Experiment 1

In a first experiment the effect of the addition of a PCV2 ORF2 subunit vaccine on the viability of a live attenuated PRRS virus vaccine was established, with or without the presence of bovine serum albumine in the final vaccine. For this the PRRS virus titer was measured (log 10 TCID50/ml) in a dilution on MA-104 cells (African green monkey kidney cells) one hour after combining the vaccines. As a control, the viability of the same PRRS virus vaccine was measured without adding the PCV2 vaccine. The results are indicated below in Table 1 for vaccines wherein the (aimed at) start titer of the PRRS virus was 4 (log 10). In the combination vaccine 0.3% (3 grams per litre vaccine) serum albumin was added. Table 2 gives the same results for vaccines wherein the (aimed at) start titer of the PRRS virus was 5 (log 10). In this latter combination vaccine also 0.3% (3 grams per litre vaccine) serum albumin was added. The results indicate that albumin has a significant effect on PRRS virus viability in the combination vaccine.

TABLE 1

Effect of PCV2 vaccine on PRRS virus viability

| Sample (PRRS start titer 4 log10) | PRRS virus viability |
|---|---|
| Control (PRRS virus vaccine) | 3.3 |
| PCV/PRRS, no albumin | 0 |
| PCV/PRRS, 0.3% albumin | 3.0 |

TABLE 2

Effect of PCV2 vaccine on PRRS virus viability

| Sample (PRRS start titer 5 log10) | PRRS virus viability |
|---|---|
| Control (PRRS virus vaccine) | 4.5 |
| PCV/PRRS, no albumin | 2.2 |
| PCV/PRRS, 0.3% albumin | 4.8 |

Experiment 2

In the second experiment different proteins were tested for their effect on the viability of PRRS virus in a PCV2/PRRS virus combination vaccine. In this experiment the combined PCV2/PRRS virus samples with a final concentration of (alleged) PRRS virus stabiliser of 1% (w/w), were tested for PRRS viability (starting titre of 5 log 10) as described under Experiment 1. For this, the stabilisers were mixed with the PRRS virus vaccine and thereafter the PCV2 vaccine was added. The following proteinaceous virus stabilisers (next to bovine serum albumin) were tested:
Vegetable peptone (Sigma Aldrich 18332-500G-F)
Vegetable peptone No 1 (Sigma Aldrich 61854-500G-F)
Vegetable peptone No 2 (Sigma Aldrich 19942-500G-F)
Soybean peptone (Sigma Aldrich 70178-100G)
Skimmed milk (Campina, The Netherlands)
Ovalbumin (Sigma Aldrich, A5253-250G)
NZ-amine (casein hydrolysate; lab product)
The results are indicated here below in Table 3.

TABLE 3

Effect of PCV2 vaccine on PRRS virus viability

| Sample | PRRS virus titer |
|---|---|
| Control (PRRS virus vaccine) | 6.4 |
| Bovine serum albumin | 6.4 |
| Vegetable peptone | 4.2 |
| Vegetable peptone No 1 | 4.3 |
| Vegetable peptone No 2 | 4.0 |
| Soybean peptone | 4.0 |
| Skimmed milk | 4.8 |
| Ovalbumin | 6.1 |
| NZ-amine | 4.3 |

It appeared that only with albumin (either of bovine or chicken egg source), the PRRS virus titer decrease could be (almost completely) prevented.

Experiment 3

Objective

The objective of this study was to evaluate efficacy and safety of PCV2/Mhyo/PRRS combination vaccines and in particular to show the effect of the addition of albumin on the PRRS efficacy. The efficacy towards protection against infection with PCV2 was evaluated by assessing anti-ORF2 serology. The efficacy against infection with *Mycoplasma hyopneumoniae* was evaluated by comparing the serological response with that of the commercially available Mhyo vaccine Porcilis® Mhyo (MSD Animal Health, Boxmeer, The Netherlands). The efficacy against an infection with PRRS virus was evaluated by assessing serology and the PRRs viraemia upon challenge with a pathogenic PRRS strain, 4 weeks post vaccination.

Experimental Design

The progeny of 10 sows was available for this study. A total of 40 animals were allotted to 4 groups of 10 piglets each. All animals were transferred to an animal facility when they were approximately 4 weeks old. Groups 1 to 4 were intradermally vaccinated using the IDAL® vaccinator into the right side of the neck. Groups 1 and 2 each received an ORF2 protein based PCV2 vaccine comprising in addition Mhyo bacterin (the same antigen as in the commercially available product Porcilis® M Hyo), and 3% ovalbumin (group 1) or no albumin (group 2). In these combination vaccines a live PRRS virus vaccine (Porcilis PRRS) was reconstituted. The vaccines used Montanide IMS 251, available from SEPPIC, France as adjuvant. Each vaccine contained 9 µg/dose of the ORF2 protein, and Mhyo antigen at 1-2 times the concentration of the M Hyo antigen in the commercially available vaccine Porcilis® M Hyo ID ONCE. The PRRS vaccine was a freeze-dried vaccine and was reconstituted immediately before administration to contain $10^{4.5}$ $TCID_{50}$ of virus per dose of 200 µl using the appropriate PCV2 vaccine or a diluent. Group 3 only received the PRRS vaccine and group 4 remained unvaccinated and served as (challenge) control. All piglets were observed daily for clinical signs. The animals were challenge-infected with pathogenic PRRS virus (type I) when they were approximately 8 weeks old (day 28). The challenge material contained (a calculated dose of) 5.3 log 10 TCID50 of the virus in 2 ml. The material was intra-nasally administered, 1 ml per nostril. At the end of the observation period (49 days after vaccination corresponding to 21 days post challenge) all pigs were sacrificed. Blood samples (via v. jugularis) were taken from all animals individually on day 0, 14, 28 (right before challenge), 31, 35, 38, 42 and 49 and tested for the presence of PRRS virus, for antibodies against PRRSV, PCV2 and Mhyo.

Results

No animals showed any clinical signs due to vaccination and rectal temperatures remained within 1.5° C. from controls. The vaccines are thus regarded safe.

Regarding Mhyo, the serological response of the combination vaccine appears to be comparable to that as obtainable with the commercially available vaccine Porcilis M Hyo (no numerical results depicted in a figure). It may thus be assumed that the vaccine protects against infection with Mhyo.

The results of the PCV2 serological response are given in FIG. 1. It appears that the two combination vaccines induce a positive anti-ORF2 antibody response which means that the vaccines induce protection against infection with wild-type PCV2.

Figure 2:
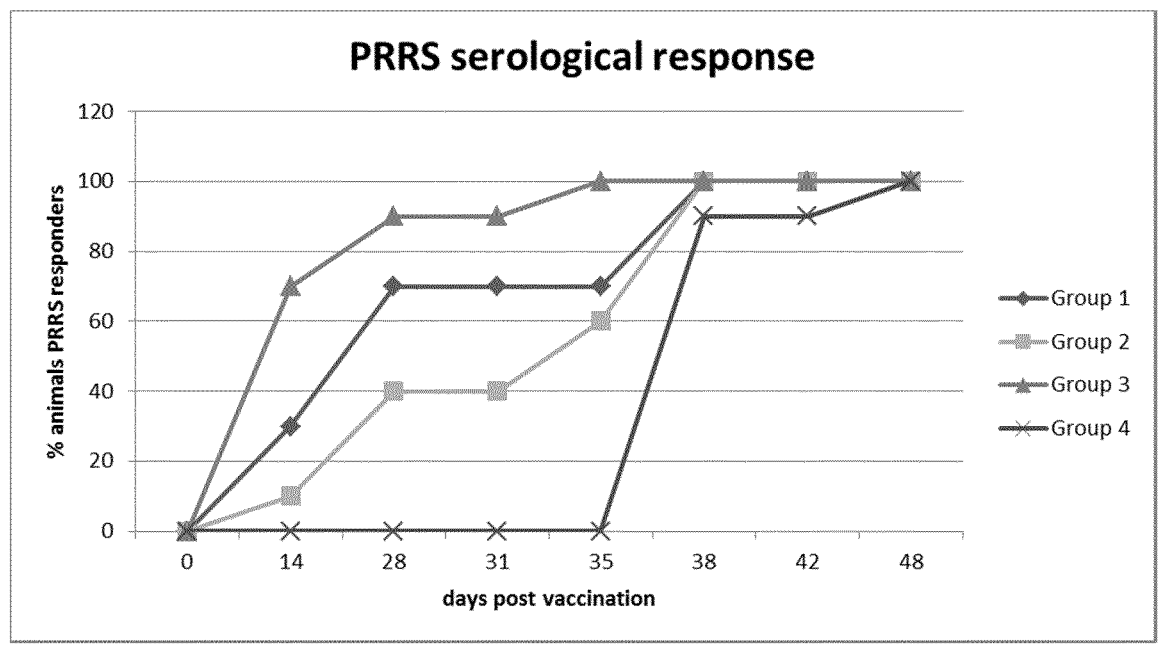
FIG. 2 is a line graph representing the PRRS serological response.
Figure 3:
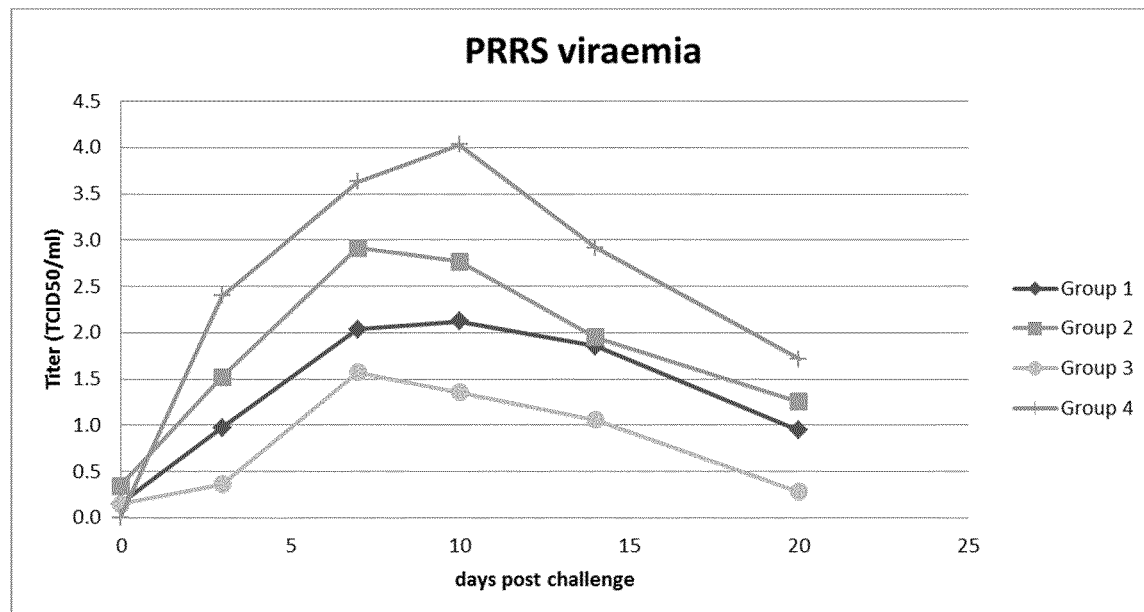
FIG. 3 is a line graph representing the PRRS viraemia data.

The results of the PRRS serological response are given in FIG. 2. It appears that the two combination vaccines, like the commercially available PRRS vaccine, induce a positive anti-PRRS antibody response before challenge. This is an indication that the vaccines provide protection against PRRS virus infection. It can also be seen that the serology was improved in the vaccine comprising the albumin. In FIG. 3 the viraemia data are given. These results are in line with the results of FIG. 2. It appears that all three vaccines provide protection against PRRS virus infection since viraemia levels are lower than the level in the control animals (group 4) at each point in time. Still, the combination vaccine comprising albumin provides better protection against challenge than the combination vaccine without the albumin.

The invention claimed is:

1. A vaccine comprising in combination a non-replicating immunogen of porcine circovirus type 2 (PCV2), a live attenuated porcine reproductive and respiratory syndrome (PRRS) virus, and albumin.

2. A vaccine of claim 1, wherein the vaccine comprises ovalbumin.

3. A vaccine of claim 1, wherein the albumin concentration is between 0.1 and 10% (w/w).

4. A vaccine of claim 1, wherein the non-replicating immunogen of PCV2 is recombinantly expressed ORF2 protein of PCV2.

5. A vaccine of claim 1, wherein the non-replicating immunogen of PCV2 is baculovirus expressed ORF2 protein of PCV2.

6. A vaccine of claim 1, wherein the vaccine comprises in addition non-replicating immunogen of *Mycoplasma hyopneumoniae*.

7. A vaccine for use in prophylactically treating an animal against an infection with porcine circovirus type 2 (PCV2), an infection with porcine reproductive and respiratory syndrome (PRRS) virus, or an infection of both PCV2 and PRRS virus, wherein the vaccine comprises in combination non-replicating immunogen of PCV2, live attenuated PRRS virus, and albumin.

8. A vaccine of claim 7, wherein said vaccine is administered into the dermis of the animal.

9. A vaccine of claim 7, wherein said vaccine is administered by a single dose.

10. A vaccine of claim 7, wherein said vaccine is administered with a needle-less vaccination device.

11. A vaccine of claim 7, wherein immunogen of PCV2 and the live attenuated PRRS virus are combined in the vaccine within 24 hours before administration.

12. A vaccine of claim 7, wherein immunogen of PCV2 and the live attenuated PRRS virus are combined in the vaccine within 6 hours before administration.

13. A vaccine of claim 11, wherein prior to combination of the immunogens, the albumin is present in combination with the immunogen of PRRS virus.

14. A method for prophylactically treating an animal against an infection with porcine circovirus type 2 (PCV2), an infection with porcine reproductive and respiratory syndrome (PRRS) virus, or an infection of both PCV2 and PRRS virus, by administrating to the animal a vaccine comprising in combination non-replicating immunogen of PCV2, live attenuated PRRS virus, and albumin.

15. A method of manufacturing a vaccine comprising the non-replicating immunogen of porcine circovirus type 2 (PCV2), the live attenuated porcine reproductive and respiratory syndrome (PRRS) virus, and albumin, for administration to an animal to prophylactically treat the animal against an infection with PCV2, an infection with PRRS virus, or an infection of both PCV2 and PRRS virus.

* * * * *

UNITED STATES PATENT AND TRADEMARK OFFICE
CERTIFICATE OF CORRECTION

| | | |
|---|---|---|
| PATENT NO. | : 10,953,084 B2 | Page 1 of 1 |
| APPLICATION NO. | : 16/086629 | |
| DATED | : March 23, 2021 | |
| INVENTOR(S) | : Sno et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 104 days.

Signed and Sealed this
Fourteenth Day of February, 2023

*Katherine Kelly Vidal*

Katherine Kelly Vidal
*Director of the United States Patent and Trademark Office*